United States Patent [19]

Jordan

[11] Patent Number: 4,601,708
[45] Date of Patent: Jul. 22, 1986

[54] AUTOMATIC INJECTION FOR SYRINGE NEEDLE, AND ASSEMBLY

[76] Inventor: Pavel Jordan, 1026 Brent Ave., So. Pasadena, Calif. 91030

[21] Appl. No.: 773,573

[22] Filed: Sep. 9, 1985

[51] Int. Cl.$^4$ ............................................. A61M 5/20
[52] U.S. Cl. ..................................................... 604/136
[58] Field of Search ................ 604/136, 134, 135, 186

[56] References Cited

U.S. PATENT DOCUMENTS

| | | | |
|---|---|---|---|
| 2,295,849 | 9/1942 | Kayden | 604/136 |
| 2,472,116 | 6/1949 | Maynes | 604/136 |
| 3,880,163 | 4/1975 | Ritterskamp | 604/136 |
| 4,261,358 | 4/1981 | Vargas et al. | 604/136 |
| 4,547,189 | 10/1985 | Moore, Jr. | 604/136 |

*Primary Examiner*—Stephen C. Pellegrino
*Attorney, Agent, or Firm*—Willie Krawitz

[57] ABSTRACT

An injector device for a syringe and assembly is disclosed which enables the user to inject a syringe needle to a predetermined depth.

The device includes a pipe union bearing upper retaining arms that are adapted to interfit with a plunger of a standard injector syringe. The pipe union is slidably mounted along an inner tube through which the syringe and needle are projected. The pipe union and an attached screw nut form upper and lower shoulders along the inner tube. The pipe union is spring loaded for movement along the inner tube, and this movement is set between the upper and lower shoulders by means of a rotatable firing hammer. The hammer fixes the pipe union and attached syringe in the upper, spring loaded position, and when triggered, the hammer releases the pipe union to the lower position and fires the syringe needle into the user. A lower adjustable tube partly encloses the inner tube, and provides a lower flat surface that contacts the user's body and enables the needle to be applied at the desired location.

9 Claims, 6 Drawing Figures

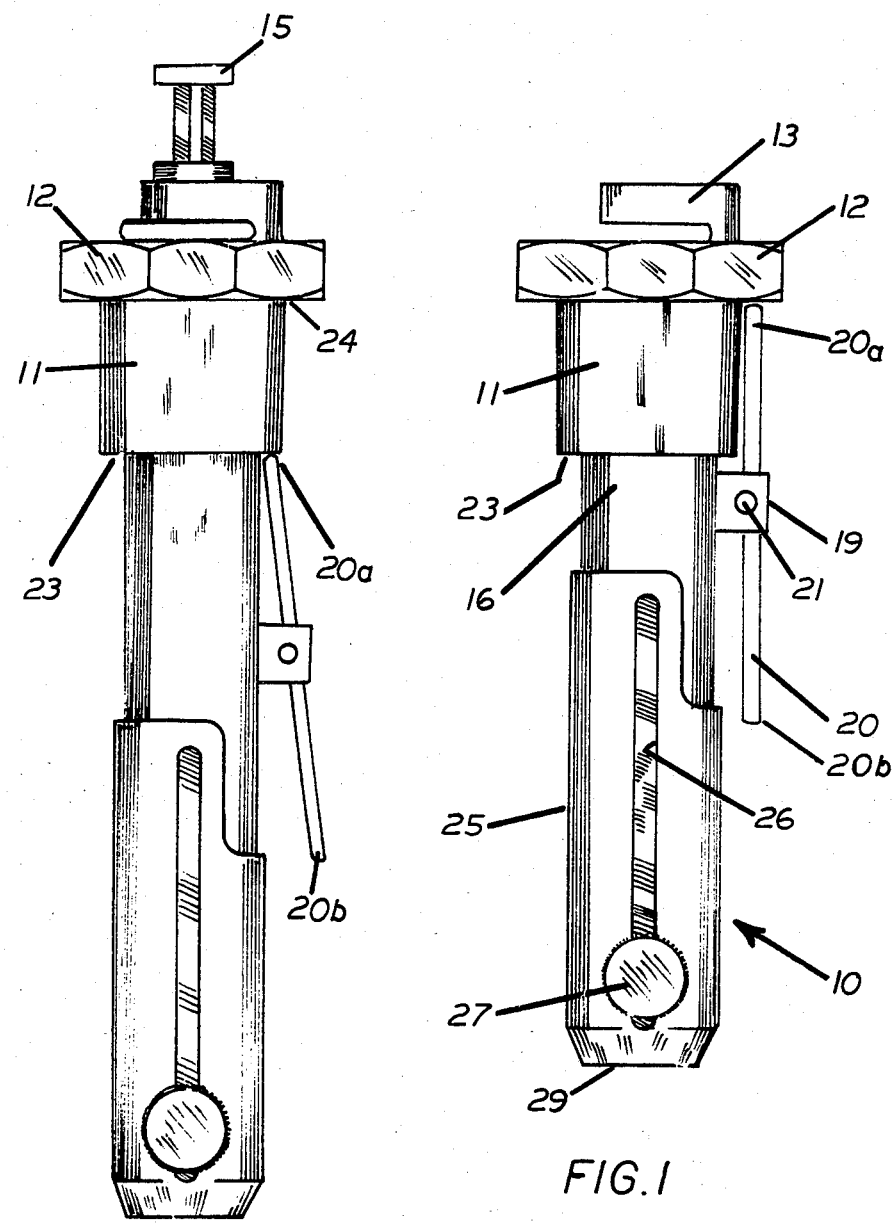

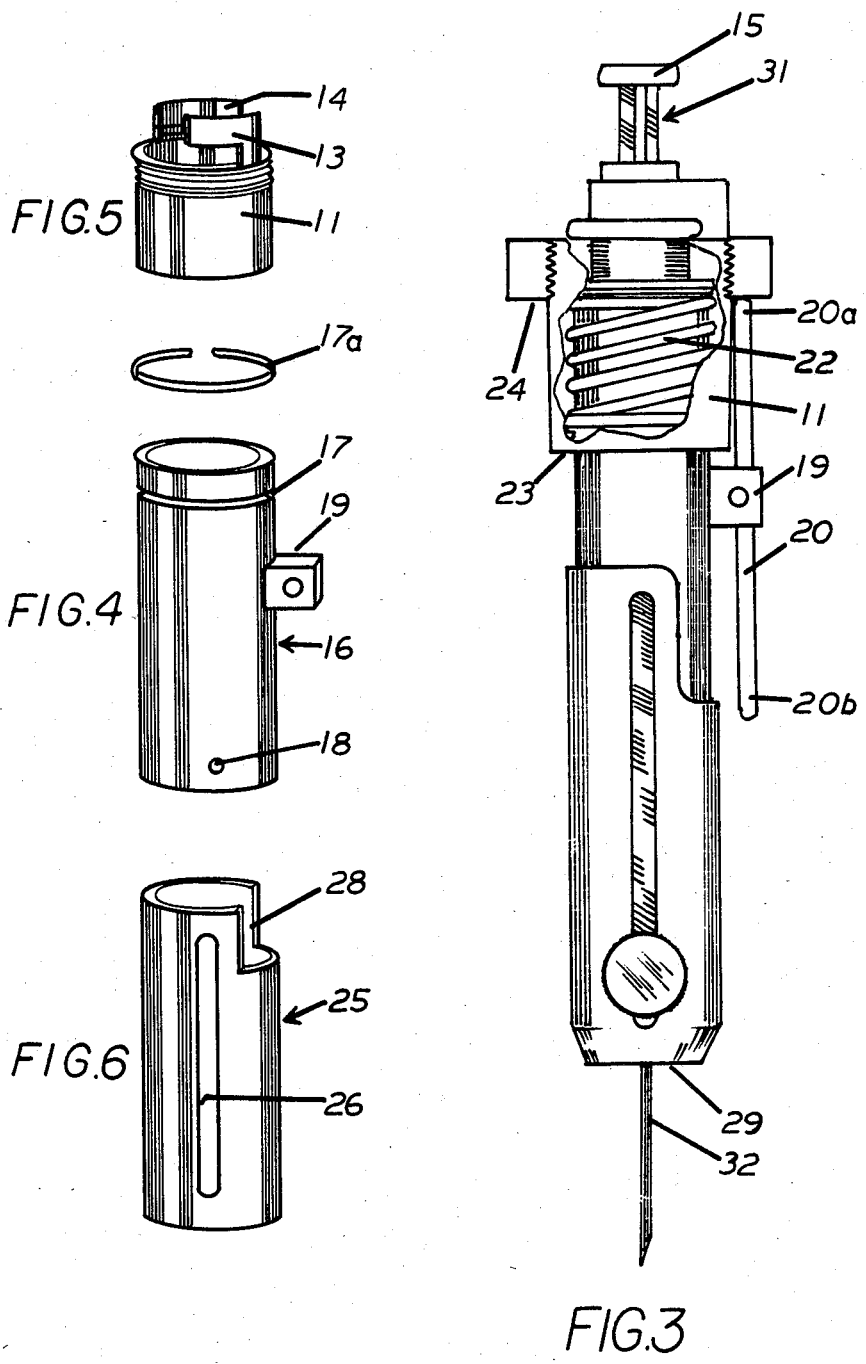

AUTOMATIC INJECTION FOR SYRINGE NEEDLE, AND ASSEMBLY

BACKGROUND OF THE INVENTION

This invention relates to a new and improved injector for a syringe needle, and an assembly therefor. More specifically, this invention relates to an injector and assembly for securing to a syringe plunger in a simple manner. The injector is adapted to fire the plunger and needle into the user at a desired angle and depth while the device is maintained in a secure position on the user's body. In addition, the device does not require viewing of the syringe needle by the user, many of whom find this objectionable.

Publications describing syringe injectors for self use are disclosed in U.S. Pat. Nos. 2,856,924; 3,702,608; 3,941,130; 3,880,163; D. 247,576; and, 4,261,358. These devices tend to be complicated in terms of number of parts, and their assembly. Also, many prior art injector devices are designed for use with only a single type, or limited few, syringe injectors. Moreover, the stocking of replacement components is expensive, so that generally the entire device is usually replaced if a component part fails or becomes worn out. In addition, some syringe injectors mount the syringe in an open position, and this is objectionable to many users.

A spring loaded injector device for a syringe and needle is desired having few component parts and a rugged construction. The device should include a trigger system that provides a distinct switching between two well defined upper and lower limits. This in turn will enable the user to preset the device for a predictable needle exposure, and hence penetration, after the injector has been fired.

THE INVENTION

According to the invention, a spring loaded injector device is provided including an upper pipe union having engaging fingers that are sized to secure a syringe plunger. The arrangement and configuration of the fingers also enables the device to accommodate most of the common commercial types of syringe plungers. The pipe union is slidably mounted along the exterior of a hollow inner tube through which the syringe and needle are projected by means of a spring loading. A collar is threaded to the upper end of the pipe union and provides a lower boundary stop for movement of the injector. At its lower end, the pipe union forms a shoulder that provides an upper boundary stop when the injector is loaded.

A pivotally moving trigger bar is mounted on the outer wall of the hollow, inner tube. In the loaded position, the trigger bar rests on the shoulder of the pipe union, and when the trigger bar has been switched to fire the injector, the trigger bar will come to rest against the collar. Thus, the distance through which the syringe needle moves is very carefully defined, and this enables the user to direct the injection to a precise site.

An outer tube is adjustably mounted on the exterior of the inner tube for controlling the maximum length of syringe needle exposure. Consequently, control of both the distance of syringe needle movement and the location of the adjustable exterior tube enables the user to employ the injector device with precision. The lower end of the exterior tube is machined flat, and this permits the user to incline the outlet (needle) end of the device against the body in a reasonably uniform manner from injection to injection.

BRIEF DESCRIPTION OF THE DRAWINGS

FIG. 1 is an external view in side elevation showing the injector device of the invention in the unloaded position;

FIG. 2 is an external view in side elevation showing the assembly of the injector and a syringe with needle in the loaded position;

FIG. 3 is an external view in side elevation, partly broken away, to show the spring loading, illustrating the assembly of the injector and syringe following firing of the injector;

FIG. 4 is an external view in side elevation, partly in perspective, showing the inner tube component of the injector device;

FIG. 5 is an external view, partly in perspective, showing the union joint component of the injector device; and, FIG. 6 is an external view, partly in perspective, showing the outer tube component of the injector device.

DESCRIPTION OF THE PREFERRED EMBODIMENTS

The injector device 10 of this invention is typically manufactured from a stainless steel such as 304–316, and is shown comprising a pipe union 11 threadably attached to a stop nut 12. Opposed curved L-shaped arms 13, 14 are formed at the upper end of the pipe union for engaging the upper end of a plunger 15 of a syringe barrel.

The tube portion 16 of the injector defines an upper, peripheral groove 17, a threaded hole 18, and a hammer holder 19 into which is mounted a hammer 20, pivoted about a pin 21. The pipe union 11 is slidably mounted over the tube portion 16 and upwardly biased by a spring 22. The pipe union 11 and tube portion 16 are connected by the spring 22 which is secured at one end of the groove 17 of the tube portion, together with a spline 17a, and along a shoulder (not shown) around the interior wall of the pipe union. The lower portion of the pipe union forms a circular, peripheral shoulder 23 around the tube portion 16, and the lower portion of the stop nut 12 forms a circular, peripheral shoulder 24 around the pipe union 11.

As shown in FIGS. 1 and 2, the outer tube 25 is adjustably mounted outwardly of the tube portion 16. The outer tube provides a slot 26 through which a screw 27 passes for fitting into the threaded hole 18. Adjustment of the outer tube 25 and the tube portion 16 relative to each other, is provided by loosening the screw 27, moving the outer tube 25 along the slot 26, and then tightening the screw into the hole 18 to secure the outer and inner tubes together. The extent of adjustment between the outer and inner tubes will determine the amount of needle projection beyond the outer tube. A cut out 28 may be provided to view the contents of the syringe, although this is not necessary for operation of the device. The end portion 29 of the outer tube is machined flat so that it can be pressed evenly against the user's skin.

In operation, the syringe 31 and attached needle 32, typically about 24–26 gauge, are loaded into the top of the injector, and then rotated so that the plunger 15 is engaged into the opposed arms 13, 14, as shown. The screw nut 12 is then rotated upwardly to secure the arms and plunger together. Thus, the screw nut performs the dual function of providing a stop shoulder, and to secure the injector. Usually, a needle cover (not shown) is employed to maintain the needle in a reasonably sterile condition, prior to use; when the injector is ready for use, the needle cover is removed. The outer tube 25 is then adjusted along slot 26 to provide the desired length of needle exposure beyond the end portion 29, and the pipe union 11 is retracted against the bias of the spring 22. The hammer 20 is then rotated until the hammer tip 20a rests under the shoulder 23 of the pipe union 11, and this will secure the injector in place and ready for firing. The injector is then placed against the injection site of the user's body, and fired by tripping the hammer end 20b. This disengages the hammer end 20a from the shoulder 23 of the pipe union 11 and causes the pipe union and attached syringe 31 and needle 32 to be thrust forwardly by the spring 27 until the hammer end 20a contacts the shoulder 24 of the stop nut 12. The needle is thereby projected beyond the end portion 29 of the outer tube 25 to a preset length, and into the user's body. The preset length is determined by the projection distance between the two shoulders 23 and 24, and by the amount of extension of the outer tube 25 relative to the inner tube 16.

The plunger is depressed to inject the desired amount of liquid, the needle is withdrawn, and the syringe and needle are removed by loosening the nut 12, and disengaging from the injector arms 13, 14; finally, the syringe and needle are discarded.

The device of the present invention employs few components that are large, sturdy, and will not deform (except possibly the spring), even during extended use. Most importantly, the device does not require the manufacture of a special associated type of syringe device since the engaging arms 13, 14 are sized to accommodate many of the standard commercial syringes for self injection.

I claim:

1. An injection device for a syringe and needle, comprising
   a. an inner tube for guiding a syringe and needle assembly therethrough, the inner tube including an outer surface and providing a hammer holder mounted on the tube surface, and a hammer rotatably mounted by the hammer holder, the hammer defining a stop end, and means for securing a spring loading element disposed on said tube;
   b. a spring loading element secured at one end of the tube;
   c. a pipe union providing upper arms for engagement with a syringe plunger, the pipe union being slidably mounted along the outer surface of the inner tube, and attached to the inner tube by the spring element, and being upwardly biased by said spring, the pipe union extending outwardly from the tube surface to define a peripheral shoulder;
   d. a stop nut mounted upwardly of the pipe union and adjacent to the upper engagement arms, and providing an outwardly extending shoulder peripherally of the outer tube surface, the stop nut being adapted for rotation to secure and release the plunger and upper arms of the pipe union; and,
   e. an outer tube surrounding a portion of the inner tube, and being adjustably mounted thereon, the outer tube defining a flat end surface for pressing against a user's body and providing a stable platform for projection of the needle therefrom; whereby: i. when the injection device is biased upwardly along the inner tube in a loaded position, the hammer at the stop end is adapted to bear against the shoulder of the pipe union and maintain the injector in the loaded position; ii. when the hammer if tripped, the union tube is released and biased downwardly by the spring, thereby projecting the attached syringe and needle in a uniform manner along the inner tube; iii. when the hammer at the stop end contacts the shoulder of the stop nut, the pipe union will be restrained from further movement; and, iv. the adjustable mounting of the outer tube along the inner tube provides a projection length of the needle beyond the flat end of the outer tube, which is uniform from injection to injection.

2. The injection device of claim 1, in which a peripheral groove is defined around the outer tube surface, and the spring loading element is secured at one end within the groove.

3. The injection device of claim 1, in which a threaded hole is provided in the inner tube, and a longitudinal slot is provided along the outer tube, the inner and outer tubes being secured by a screw which passes through the slot and into the hole. the inner and outer tubes being adapted to move relative to each other by loosening the screw and adjustment of the tubes along the slot.

4. An assembly of an injection device and a syringe and needle, comprising:
   a. a syringe and needle, including a syringe plunger element;
   b. an inner tube for guiding the syringe and needle therethrough, the inner tube including an outer surface and providing a hammer holder mounted on the tube surface, and a hammer rotatably mounted by the hammer holder, the hammer defining a stop end, and means for securing a spring loading element disposed on said tube;
   c. a spring loading element secured at one end of the tube;
   d. a pipe union providing upper arms for engagement with a syringe plunger, the pipe union being slidably mounted along the outer surface of the inner tube, and attached to the inner tube by the spring element, and being upwardly biased by said spring, the pipe union extending outwardly from the tube surface to define a peripheral shoulder;
   e. a stop nut mounted upwardly of the pipe union and adjacent to the upper engagement arms, and providing an outwardly extending shoulder peripherally of the outer tube surface, the stop nut being adapted for rotation to secure and release the plunger and upper arms of the pipe union; and,
   f. an outer tube surrounding a portion of the inner tube, and being adjustably mounted thereon, the outer tube defining a flat end surface for pressing against a user's body and providing a stable platform for projection of the needle therefrom; whereby: i. when the injection device is biased upwardly along the inner tube in a loaded position, the hammer at the stop end is adapted to bear against the shoulder of the pipe union and maintain the injector in the loaded position; ii. when the hammer is tripped, the union tube is released and biased downwardly by the spring, thereby projecting the attached syringe and needle in a uniform manner along the inner tube; iii. when the hammer at the stop end contacts the shoulder of the stop nut, the pipe union will be restrained from further movement; and, iv. the adjustable mounting of the outer tube along the inner tube provides a projection length of the needle beyond the flat end of the outer tube, which is uniform from injection to injection.

5. The injection device of claim 4, in which a peripheral groove is defined around the outer tube surface, and the spring loading element is secured at one end within the groove.

6. The injection device of claim 4, in which a threaded hole is provided in the inner tube, and a longitudinal slot is provided along the outer tube, the inner and outer tubes being secured by a screw which passes through the slot and into the hole, the inner and outer tubes being adapted to move relative to each other by loosening the screw and adjustment of the tubes along the slot.

7. A method for injecting a syringe and needle included in an assembly of an injection device, the assembly comprising:
   a. a syringe and needle, including a syringe plunger element;
   b. an inner tube for guiding the syringe and needle therethrough, the inner tube including an outer surface and providing a hammer holder mounted on the tube surface, and a hammer rotatably mounted by the hammer holder, the hammer defining a stop end, and means for securing a spring loading element disposed on said tube;
   c. a spring loading element secured at one end of the tube;
   d. a pipe union providing upper arms for engagement with a syringe plunger, the pipe union being slidably mounted along the outer surface of the inner tube, and attached to the inner tube by the spring element, and being upwardly biased by said spring, the pipe union extending outwardly from the tube surface to define a peripheral shoulder;
   e. a stop nut mounted upwardly of the pipe union and adjacent to the upper engagement arms, and providing an outwardly extending shoulder peripherally of the outer tube surface, the stop nut being adapted for rotation to secure and release the plunger and upper arms of the pipe union; and,
   f. an outer tube surrounding a portion of the inner tube, and being adjustably mounted thereon, the outer tube defining a flat end surface for pressing against a user's body and providing a stable platform for projection of the needle therefrom; the method comprising: i. upwardly biasing the injection device along the inner tube in a loaded position, the hammer at the stop end being adapted to bear against the shoulder of the pipe union and maintain the injector in the loaded position; ii. tripping the hammer, the union tube being released and biased downwardly by the spring, thereby projecting the attached syringe and needle in a uniform manner along the inner tube; iii. contacting the hammer at the stop end with the shoulder of the stop nut, thereby restraining the pipe union from further movement; and, providing a projection length of the needle beyond the flat end of the outer tube, which is uniform from injection to injection, by means of the adjustable mounting of the outer tube along the inner tube.

8. The method of claim 7, in which a peripheral groove is defined around the outer tube surface, and the spring loading element is secured at one end within the groove.

9. The method of claim 8, in which a threaded hole is provided in the inner tube, and a longitudinal slot is provided along the outer tube, the inner and outer tubes being secured by a screw which passes through the slot and into the hole, the inner and outer tubes being adapted to move relative to each other by loosening the screw and adjustment of the tubes along the slot.

* * * * *